United States Patent
Guglielmotti et al.

(10) Patent No.: US 6,534,534 B1
(45) Date of Patent: Mar. 18, 2003

(54) PHARMACEUTICAL COMPOSITION ACTIVE IN REDUCING PRODUCTION OF MCP-1 PROTEIN

(75) Inventors: Angelo Guglielmotti, Rome (IT); Alberto Mantovani, Milan (IT)

(73) Assignee: Aziende Chimiche Riunite Angelini Francesco A.C.R.A.F. S.p.A., Rome (IT)

( * ) Notice: Subject to any disclaimer, the term of this patent is extended or adjusted under 35 U.S.C. 154(b) by 0 days.

(21) Appl. No.: 09/463,666
(22) PCT Filed: Jul. 22, 1998
(86) PCT No.: PCT/EP98/04924
§ 371 (c)(1),
(2), (4) Date: Apr. 27, 2000
(87) PCT Pub. No.: WO99/04770
PCT Pub. Date: Feb. 4, 1999

(30) Foreign Application Priority Data

Jul. 28, 1997 (IT) ......................................... MI97A1789

(51) Int. Cl.$^7$ ............................................ A61K 31/415
(52) U.S. Cl. ..................................................... 514/403
(58) Field of Search ......................................... 514/403

(56) References Cited

U.S. PATENT DOCUMENTS 5,571,713 A 11/1996 Lyle et al.

FOREIGN PATENT DOCUMENTS

| EP | 0 382 276 | 8/1990 |
| EP | 0 510 748 | 10/1992 |
| WO | WO 97/16185 | 5/1997 |

OTHER PUBLICATIONS

L. Saso, et al., The Journal of Rheumatology, vol. 19, No. 12, pp. 1859–1867, "Abnormal Glycosylation of Hemopexin in Arthritic Rats can be Blocked by Bindarit", Dec. 1992.

V. Cioli, et al., The Journal of Rheumatology, vol. 19, No. 11, pp. 1735–1742, "A New Protein Antidenaturant Agent, Bindarit, Reduces Secondary Phase of Adjuvant Arthritis in Rats", Nov. 1992.

A. Guglielmotti, et al., Biochemistry and Molecular Biology International, vol. 29, No. 4, pp. 747–756, "Chronic Inflammatory Response in the Rat can be Blocked by Bindarit", Mar. 1993.

L. Saso, et al., Clinical Chemistry, vol. 38, No. 6, p. 1073, "Abnormal Glycosylation of Selected Glycoproteins During Chronic Inflammatory Conditions can be Reversed by Bindarit", 1992, (English Abstract only).

D. Corna, et al., J. Am. Soc. Nephrol., vol. 9, p. 473A, "Bindarit Limits Renal Disease and Prolongs Survival in Murine Lupus Autoimmune Disease", 1997, (English Abstract only).

A. Guglielmotti, et al., J. Am. Soc. Nephrol., vol. 9, p. 470A, "Bindarit Effects on MCP-1 and IL-6: Potential Mechanism for Renal Injury Protection", 1997, (English Abstract only).

S.L. Kunkel, et al., Journal of Leukocyte Biology, vol. 59, No. 1, pp. 6–12, "The Role of Chemokines in Inflammatory Joint Disease", 1996.

Berkow, et al., The Merck Manual of diagnosis and therapy, Immunology: Allergic Disorders, pp. 319–329, 1987.

*Primary Examiner*—Sreeni Padmanabhan
*Assistant Examiner*—Mojdeh Bahar
(74) *Attorney, Agent, or Firm*—Oblon, Spivak, McClelland, Maier & Neustadt, P.C.

(57) ABSTRACT

The present application relates to a method of treating atherosclerosis by administering to a patient a compound of formula:

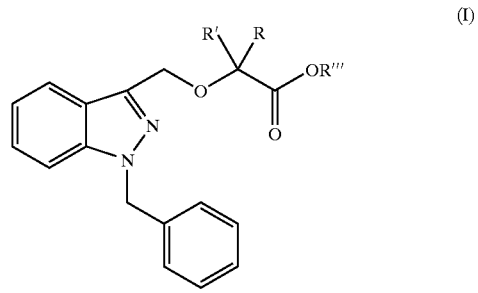

(I)

and/or salts thereof with pharmaceutically acceptable organic or inorganic bases.

4 Claims, No Drawings

PHARMACEUTICAL COMPOSITION ACTIVE IN REDUCING PRODUCTION OF MCP-1 PROTEIN

The present application is the National Stage under 35 U.S.C. 371 of PCT/EP98/04924, filed Jul. 22, 1998, which designated the United States and was published under PCT Article 21(2) in English.

The present invention relates to use of indazol methoxyalkanoic acids for preparing a pharmaceutical composition active in the treatment of disorders characterized by production of MCP-1 protein.

European patent EP-B-0 382 276 describes a compound having the formula:

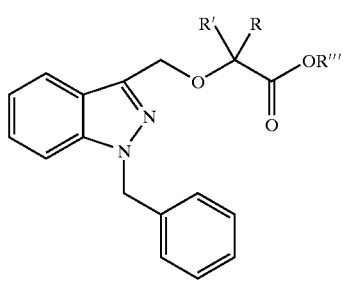

wherein
R and R', the same as or different from each other, are H or an alkyl having from 1 to 5 carbon atoms,
R''' is H or an alkyl having from 1 to 4 carbon atoms,
and, when R''' is H, salts thereof with pharmaceutically acceptable organic or inorganic bases.

The above-mentioned patent additionally specifies that the compound having the formula (I) possesses an analgesic activity.

Furthermore, European patent EP-B-0 510 748 describes the use of the compound having the formula (I) for preparing a pharmaceutical composition active in the treatment of autoimmune diseases.

It has now been found that the compound having the formula (I) is also active in reducing production of MCP-1 protein.

As already known, MCP-1 protein (Monocyte Chemotactic Protein-1) is a chemokine belonging to the β subfamily of the chemokines. It possesses a strong chemotactic activity for monoctyes and also acts on T lymphocytes, mastocytes and basophils.

Other chemokines belonging to the β subfamily are, for example: MCP-2 (Monocyte Chemotactic Protein-2), MCP-3, MCP4, MIP-1α and MIP-1β, RANTES and protein 1309.

The β subfamily differs in structure from the a subfamily; in fact, whilst the first two cysteines of the chemokines of the a subfamily are separated by an interposed amino acid, the first two cysteines of the β subfamily are adjacent to each other. MCP-1 is produced by several types of cells (leucocytes, platelets, fibroblasts, endothelial cells).

Of all the known chemokines, MCP-1 shows the highest specificity in respect of monocytes and macrophages, for which it is not only an attracting factor but also a stimulus of activation, thus inducing a process of production of superoxides and arachidonic acid, as well as being a stimulus of amplification of phagocytic activity.

Secretion of chemokines in general and especially of MCP-1 is typically induced by numerous factors such as, for example, interleukin-1 (IL-1), interleukin-2 (IL-2), TNFα (Tumor Necrosis Factor α), γ-interferon and bacterial lipopolysaccharide (LPS).

In the human, MCP-1 has been found in a large number of diseases with acute or chronic course not classified in homogeneous categories by traditional medicine: for example, interstitial lung disorders (ILD), vasculitis and atherosclerosis.

In interstitial lung disorders, MCP-1 released by pulmonary endothelial cells, attracts and activates competent cells with consequent release of mediators which damage the alveolar structures of the lung.

In vasculitis, MCP-1 is released by the endothelial cells of the vasa following harmful stimuli and attracts and activates monocytes and other cell types which become responsible for damage to the vascular wall.

In atherosclerosis, MCP-1 is produced by the vascular endothelium following damage to the vascular smooth muscle cells. MCP-1 attracts monocytes which initially adhere to the arterial wall and then migrate through the walls, contributing to formation of atheroma by stimulating proliferation of smooth muscle cells.

The therapies currently used in these disorders, because they act upstream of the pathological phenomena, are aspecific and very often have numerous and at times serious side effects.

The above-mentioned therapies, moreover, only enable temporary remission of the pathological phenomena to be obtained and their high toxicity prevents their use for prolonged periods of the kind necessary on the other hand in diseases of chronic type.

For atherosclerosis, in particular, the drugs currently used only act on certain factors which contribute to formation of the atheroma, such as hypercholesterolaemia or hypertension, whilst having no effect on the target of the pathological process, i.e. the vascular wall.

Chemotactic factors in general and MCP-1 in particular are also very important in cases where complications occur following surgical interventions such as, for example, angioplasty, atherectomy, circulatory recovery techniques, transplants, organ replacements, tissue replacements and prosthetic implants. Onset of such complications often makes it necessary for the patient to undergo further intensive therapies or even a new intervention.

U.S. Pat. No. 5,571,713 claims a composition comprising an MCP-1 antisense oligonucleotide for in vitro inhibition of production of MCP-1 by mononuclear human cells and smooth muscle.

There is therefore still a strong need for a pharmaceutical composition which is effective in the treatment of disorders characterized by production of MCP-1, e.g. atherosclerosis, vasculitis, interstitial lung disorders due to postoperative complications of cardiovascular surgery, in transplants or organ or tissue replacements and in prosthetic implants.

The object of the present invention is therefore use of a compound having the formula

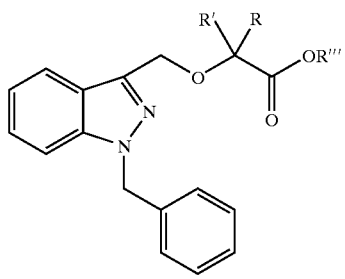

(I)

where
- R and R', the same as or different from each other, are H or an alkyl having from 1 to 5 carbon atoms,
- R''' is H or an alkyl having from 1 to 4 carbon atoms, and, when R''' is H, salts thereof with pharmaceutically acceptable organic or inorganic bases, for preparing a pharmaceutical composition for the treatment of a disorder selected from the group comprising atherosclerosis, vasculitis, interstitial lung disorders, postoperative complications in cardiovascular surgery, in transplants or organ or tissue replacements and in prosthetic implants, and characterized by an increased production of MCP-1 protein.

Preferably R''' is H, whilst R=R'=$CH_3$; this product is hereinafter called "bindarit".

Preferably the pharmaceutical compositions according to the present invention are prepared in suitable dosage forms comprising an effective dose of at least one compound having the formula (I) or a salt thereof with a pharmaceutically acceptable base and at least one pharmaceutically acceptable inert ingredient.

Examples of suitable dosage forms are tablets, capsules, coated tablets, granules, solutions and syrups for oral administration; medicated plaster patches for transdermal administration; suppositories for rectal administration and sterile solutions for administration by the injectable, aerosol or ophthalmic routes.

Further suitable dosage forms are slow release and liposome based forms, for either the oral or the injectable routes.

The dosage forms may also contain other conventional ingredients, for example: stabilising preservatives, surfactants, buffers, salts for regulation of osmotic pressure, emulsifiers, sweeteners, coloring agents, flavourings, and the like.

If required by particular therapies, the pharmaceutical composition according to the present invention may contain other pharmacologically active ingredients whose concomitant administration is therapeutically useful.

The amount of compound having the formula (I) or of a salt thereof with a pharmaceutically acceptable base in the pharmaceutical composition according to the present invention may vary within a wide range depending on known factors such as, for example, the type of disease to be treated, the severity of the disease, the patient's body weight, the dosage form, the chosen administration route, the number of daily administrations and the efficacy of the selected compound having the formula (I). The optimum amount can nevertheless easily and routinely be determined by a person skilled in the art.

Typically, the amount of compound having the formula (I) or of a salt thereof with a pharmaceutically acceptable base in the pharmaceutical composition according to the present invention will be such that it ensures an administration level of from 1 to 100 mg/kg/day. Preferably the administration level is of from 5 to 50 mg/kg/day or still more preferably of from 2 to 20 mg/kg/day.

The dosage forms of the pharmaceutical composition according to the present invention may be prepared according to techniques which are known to the pharmaceutical chemist, comprising mixing, granulation, compression, dissolution, sterilization and the like.

The following examples are intended to illustrate the present invention without limiting it in any way.

EXAMPLE 1

Effect of Bindarit on Production of MCP-1

The capability of bindarit to reduce production of MCP-1 by leucocytes (PBMC) stimulated by LPS was evaluated. White blood cells were isolated by centrifugation on a Ficoll gradient and then stimulated with LPS (100 ng/ml) for 24 hours in the presence or absence of scalar concentrations of bindarit. The supernatant fluid was collected at the end and levels of MCP-1 were measured by means of a specific immunoenzymatic test.

Table 1 shows the results obtained.

TABLE 1

| Bindarit ($\mu$g/ml) | 0 | 25 | 50 | 100 |
|---|---|---|---|---|
| MCP-1 (ng/ml) | 2.7 ± 0.51 | 1.5 ± 0.38* | 1.6 ± 0.18* | 0.8 ± 0.04* |
| IL-8 (ng/ml) | 38 ± 4.52 | 30 ± 5.20 | 37 ± 5.36 | 27 ± 5.8 |

*$p < 0.01$.

Table 1 shows that bindarit significantly reduces production of MCP-1 induced by LPS without substantially influencing levels of IL-8 produced.

EXAMPLE 2

Effect of Bindarit on Cell Attraction in the Mouse "Air Pouch"

The action of bindarit was studied in an experimental model in the mouse, the said model being characterized by production of MCP-1, cell infiltration and formation of exudate. Mice were fed ad libitum with a standard diet for rodents or with the same diet with addition of bindarit (0.5%) for 18 days. On the twelfth day, under ether anaesthesia, sterile air (5 ml) was injected under the dorsal skin of the mice to form a sac. On the fifteenth day, again under ether anaesthesia, further sterile air (5 ml) was injected into the pre-formed sac. On the eighteenth day, a sterile physiological solution (1 ml) was injected into the sac thus obtained, or an irritant (1 ml). The said irritant was carrageen (1%) or IL-1 (40 ng). After 5 hours for IL-1, or 24 hours for carrageen, the mice were sacrificed by asphyxia with $CO_2$. The exudate which had developed was collected and used for the leucocyte count and for measurement of the mediators produced.

Tables 2 and 3 show the results obtained.

TABLE 2

| | Carrageen | | IL-1 | |
| --- | --- | --- | --- | --- |
| | Exudate (ml) | Leucocytes | Exudate (ml) | Leucocytes |
| Control | 0.95 ± 0.30 | 11.2 ± 2.25 | 1.05 ± 0.05 | 11.8 ± 2.43 |
| Bindarit | 0.90 ± 0.08 | 4.5 ± 0.64** | 1.00 ± 0.01 | 7.5 ± 2.21* |

*$p < 0.05$; **$p < 0.01$.

Table 2 shows that mice treated with bindarit present a significant reduction of number of infiltrated cells (leucocytes) without presenting a reduction of volume of exudate collected.

TABLE 3

| | Polymorphonucleates (%) | Monocytes (%) |
| --- | --- | --- |
| Control + IL-1 | 74 | 26 |
| Bindarit + IL-1 | 94 | 6 |

Table 3 shows that the effect of bindarit on cell population leads to a reduction of percentage of monoctyes attracted in the sac due to the effect produced on MCP-1.

What is claimed is:

1. A method of treatment for atherosclerosis, comprising administering to a patient suffering from atherosclerosis an effective MCP-1 protein reducing amount of a compound of formula

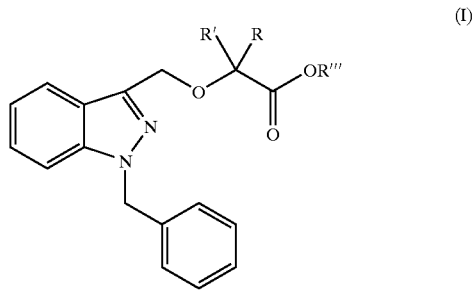

(I)

wherein
R and R' are the same or different from each other and are H or an alkyl having from 1 to 5 carbon atoms;
R''' is H or an alkyl having from 1 to 4 carbon atoms; and
when R''' is H, salts thereof with pharmaceutically acceptable organic or inorganic bases.

2. The method according to claim 1, wherein R''' is H.
3. The method according to claim 1, wherein R is methyl.
4. The method according to claim 1, wherein R' is methyl.

* * * * *

UNITED STATES PATENT AND TRADEMARK OFFICE
CERTIFICATE OF CORRECTION

PATENT NO. : 6,534,534 B1 Page 1 of 1
DATED : March 18, 2003
INVENTOR(S) : Guglielmotti et al.

It is certified that error appears in the above-identified patent and that said Letters Patent is hereby corrected as shown below:

Title page,
Item [30], Foreign Application Priority Data should read:
-- [30]  Foreign Application Priority Data
    Jul. 28, 1997  (IT)............................ MI97A01789 --

Signed and Sealed this

Twenty-second Day of July, 2003

JAMES E. ROGAN
*Director of the United States Patent and Trademark Office*